United States Patent
Shinohara et al.

(10) Patent No.: US 6,821,271 B2
(45) Date of Patent: Nov. 23, 2004

(54) DISPOSABLE UNDERGARMENT

(75) Inventors: Junji Shinohara, Kagawa-ken (JP); Hidefumi Goda, Kagawa-ken (JP); Hirotomo Mukai, Kagawa-ken (JP)

(73) Assignee: Uni-Charm Corporation, Ehine-ken (JP)

( * ) Notice: Subject to any disclaimer, the term of this patent is extended or adjusted under 35 U.S.C. 154(b) by 156 days.

(21) Appl. No.: 09/990,263

(22) Filed: Nov. 23, 2001

(65) Prior Publication Data

US 2002/0068919 A1 Jun. 6, 2002

(30) Foreign Application Priority Data

Nov. 24, 2000 (JP) ........................................ 2000-357938

(51) Int. Cl.[7] .............................................. A61F 13/15
(52) U.S. Cl. ............................. 604/385.27; 604/385.24; 604/385.26
(58) Field of Search ....................... 604/385.27, 385.24, 604/595.26, 385.01, 315.23, 385.25

(56) References Cited

U.S. PATENT DOCUMENTS

| | | | | |
|---|---|---|---|---|
| 5,188,627 A | * | 2/1993 | Igaue et al. | 604/385.27 |
| 5,779,689 A | * | 7/1998 | Pfeifer et al. | 604/385.25 |
| 5,830,203 A | | 11/1998 | Suzuki et al. | |
| 6,013,065 A | * | 1/2000 | Suzuki et al. | 604/385.27 |
| 6,210,386 B1 | * | 4/2001 | Inoue | 604/385.13 |
| 6,464,677 B1 | * | 10/2002 | Noguchi et al. | 604/385.27 |

FOREIGN PATENT DOCUMENTS

| | | | |
|---|---|---|---|
| EP | 0692233 | * 1/1996 | ........... A61F/13/15 |
| EP | 0 823 846 | 9/2000 | |
| WO | WO 00/02511 | 1/2000 | |
| WO | WO 01/85080 | 11/2001 | |

OTHER PUBLICATIONS

Japanese Patent Abstract—Publication No. 08024291, Published Jan. 30, 1996.
Japanese Patent Publication No. 1996–24291 A, Published Jan. 30, 1996.

* cited by examiner

Primary Examiner—John J. Calvert
Assistant Examiner—Jacqueline Stephens
(74) Attorney, Agent, or Firm—Lowe Hauptman Gilman & Berner, LLP

(57) ABSTRACT

A disposable undergarment includes first, second and third elastic members. The first elastic members have first both side portions extending in a longitudinal direction and a first middle portion extending across a crotch region. A second elastic member has second both side portions and a middle portion extending across the crotch region. The third elastic members have first connecting portions merged into the first both side portions and second connecting portions extending to be merged into the second both side portions. By such an arrangement, tensile stress of the third elastic member can be adequately utilized to keep the undergarment in tight contact with the wearer's thigh.

7 Claims, 8 Drawing Sheets

DISPOSABLE UNDERGARMENT

BACKGROUND OF THE INVENTION

This invention relates to disposable undergarments adapted for absorption and containment of excretion and more particularly to disposable undergarments such as a diaper, training pants, incontinence pants or the like.

Japanese Patent Application Publication No. 1996-24291A describes a disposable pants-type diaper comprising a liquid-pervious topsheet, a liquid-impervious backsheet and a liquid-absorbent core disposed between these two sheets so as to configure, in a longitudinal direction, a front waist region, a rear waist region and a crotch region extending between these two waist regions. The front and rear waist regions are connected to each other along transversely opposite side edge portion of these front and rear waist regions to define a waist-opening and a pair of leg-openings.

In the known diaper, the crotch region has a pair of transversely opposite side edge portions curving inward transversely to define peripheral edge portions of the respective leg-openings. The diaper is provided with a first elastic member attached under tension to the diaper so as to extend between front ends of the respective opposite side edge portions and to describe a circular arc which is convex rearward in the longitudinal direction and a second elastic member attached under tension to the diaper so as to extend between rear ends of the respective opposite side edge portions and to describe a circular arc which is convex forwardly in the longitudinal direction. The first and second elastic members respectively comprise side portions extending in the vicinity of the front and rear ends of the transversely opposite side edge portions and middle portions spaced in the longitudinal direction from each other and extending across the crotch region. Between the first and second elastic members, there are provided with a pair of third elastic members extending in the longitudinal direction along the transversely opposite side edge portions and bonded under tension to the diaper. The third elastic members intersect the middle portions of the first and second elastic members.

With this diaper put on the wearer's body, the elastic members continuously extend along the peripheral edge portions of the respective leg-openings, so the wearer's thighs are fully and tightly surrounded by the first-third elastic members although the first and second elastic members are spaced in the longitudinal direction from each other in the crotch region. Therefore, there is no anxiety that leakage of excretion might occur in the crotch region.

In the case of the diaper disclosed in the above-identified Publication, the third elastic members spaced in the transverse direction from each other in the crotch region rectilinearly extend along the transversely opposite side edge portions in the longitudinal direction. With a consequence, the third elastic members are not able to extend in a thigh-surrounding direction as the diaper is worn thereby to surround the wearer's thighs. Thus, tensile stress of the third elastic members is not effective in the thigh-surrounding direction and efficiently used to fit the diaper around the wearer's thighs.

In addition, zones of the transversely opposite side edge portions extending from the vicinity of respective branching points between the side portions and the middle portions to the vicinity of the front and rear ends are inevitably apt to be spaced apart from the wearer's skin. These zones should be kept in close contact with the thighs using any effective means. However, none of such means is disclosed in the above-identified Publication.

SUMMARY OF THE INVENTION

It is an object of this invention to provide a disposable undergarment improved so that the tensile stress of the third elastic members may be adequately utilized to keep the above described zones of the transversely opposite side edge portions in close contact with the wearer's thighs and to make the undergarment fit around the wearer's thighs.

According to this invention, there is provided a disposable undergarment comprising a front waist region, a rear waist region and a crotch region extending between these waist regions, a pair of leg-openings defined at transversely opposite side edge portions of the crotch region, stretchable elastic members associated with the leg-openings which comprise a first elastic member extending substantially in a circular arc from a vicinity of respective front ends of the transversely opposite side edge portions rearward, a second elastic member extending substantially in a circular arc from a vicinity of respective rear ends of the transversely opposite side edge portions forward and third elastic members extending in the longitudinal direction along the transversely opposite side edge portions between the first and second elastic members.

The first elastic member has first both side portions extending in the vicinity of the respective front ends of the transversely opposite side edge portions and a first middle portion extending across the crotch region. The second elastic member has second both side portions extending in the vicinity of the rear ends of the transversely opposite side edge portions and a second middle portion spaced rearward in the longitudinal direction from the first middle portion by a given dimension and extending across the crotch region. The third elastic members respectively extend along the transversely opposite side edge portions so as to describe circular arcs which are convex inward and have first connecting portions extending from a vicinity of respective branching points between the first both side portions and the first middle portion and merged into the first both side portions and second connecting portions which extend from the vicinity of respective branching points between the second both side portions and the second middle portion and merged into the second both side portions According to one preferred embodiment of this invention tensile stress of zones in which the first and second both side portions overlap the first and second connecting portions is higher than that of the remaining zone in which the first-third elastic members extend.

According to another preferred embodiment of this invention, the undergarment is a disposable diaper comprising a liquid-pervious topsheet, a liquid-impervious backsheet and a liquid-absorbent core disposed between these sheets.

According to still another preferred embodiment of this invention, the undergarment is a disposable diaper comprising a liquid-absorbent panel including a liquid-absorbent core disposed between a liquid-pervious topsheet and a leak-barrier sheet, and a liquid-impervious backsheet defining the front and rear waist regions and the crotch region, the panel extending across the crotch region in the longitudinal direction and being joined to inner surface of the backsheet with the leak-barrier sheet lying therebetween, the first and second elastic members being attached to the backsheet, and the third elastic members are attached to transversely opposite side edge portions of the panel extending along the transversely opposite side edge portions of the crotch region.

DETAILED DESCRIPTION OF THE PREFERRED EMBODIMENTS

Details of a disposable diaper according to this invention will be more fully understood from the description given hereunder with reference to the accompanying drawings.

Figure 1:
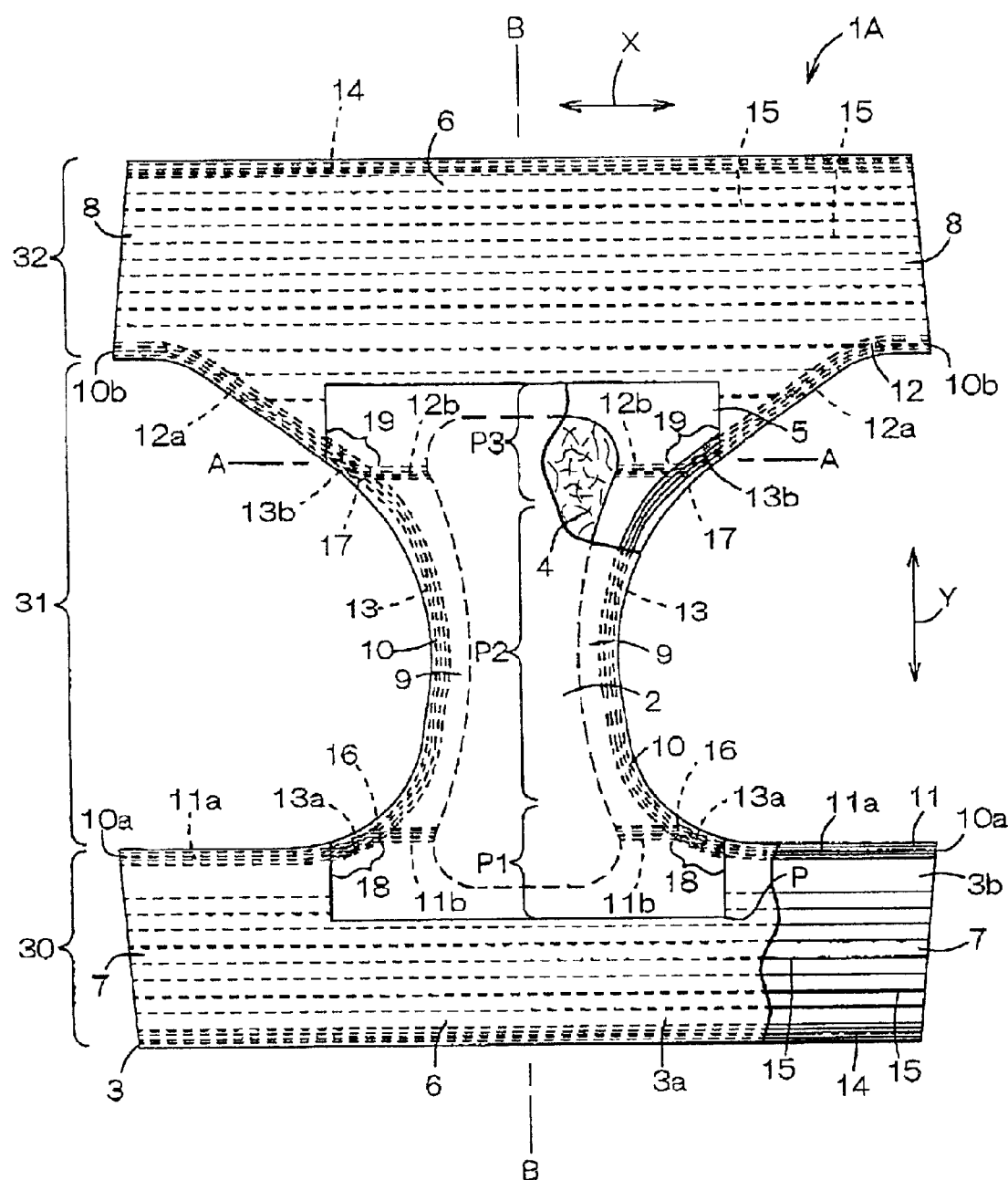
FIG. 1 is a partially cutaway plan view showing a diaper as before it is shaped in pants-type.
Figure 2:
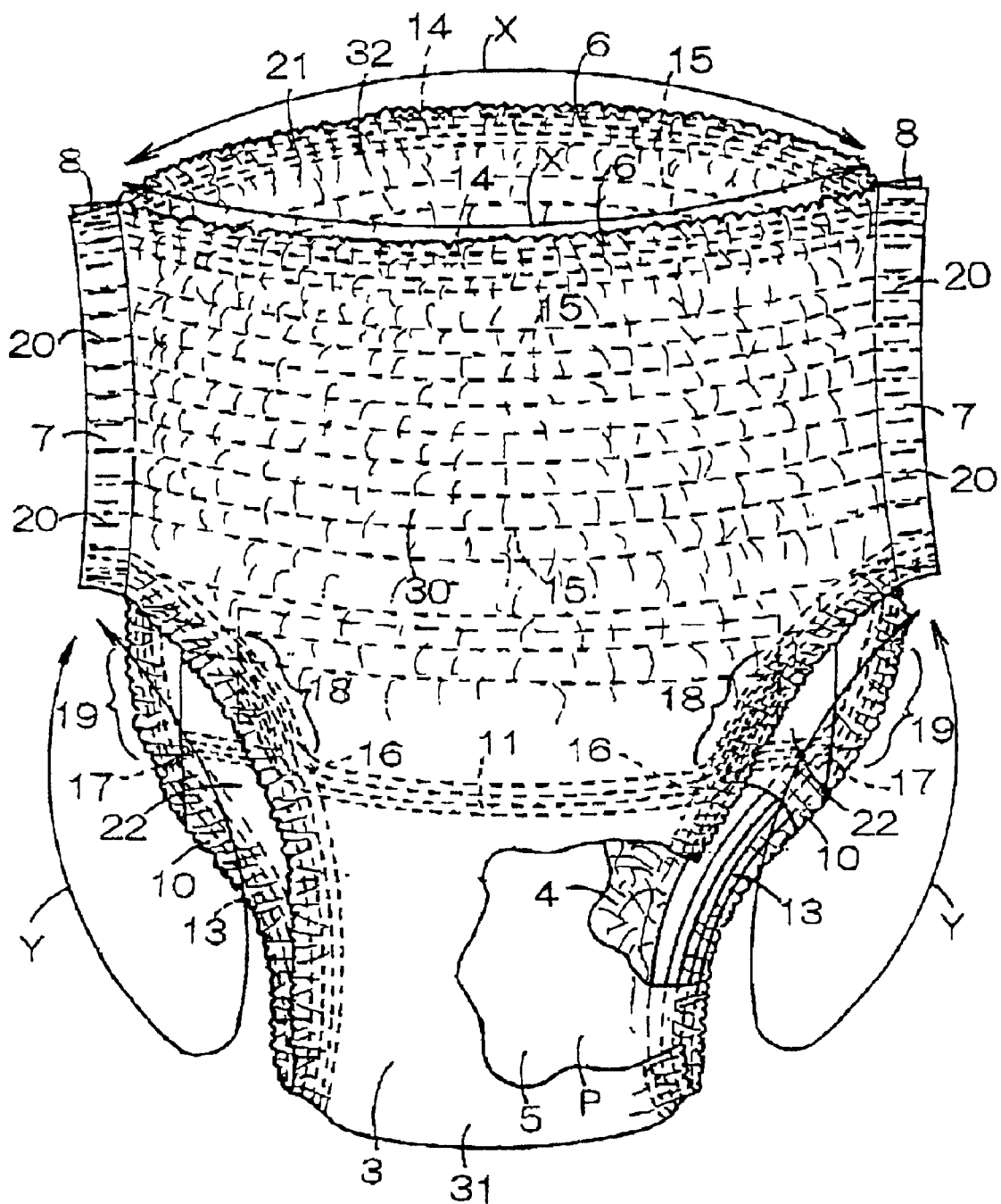
FIG. 2 is a partially cutaway perspective view showing the diaper shaped from the state of FIG. 1 into pants-type.
Figure 3:
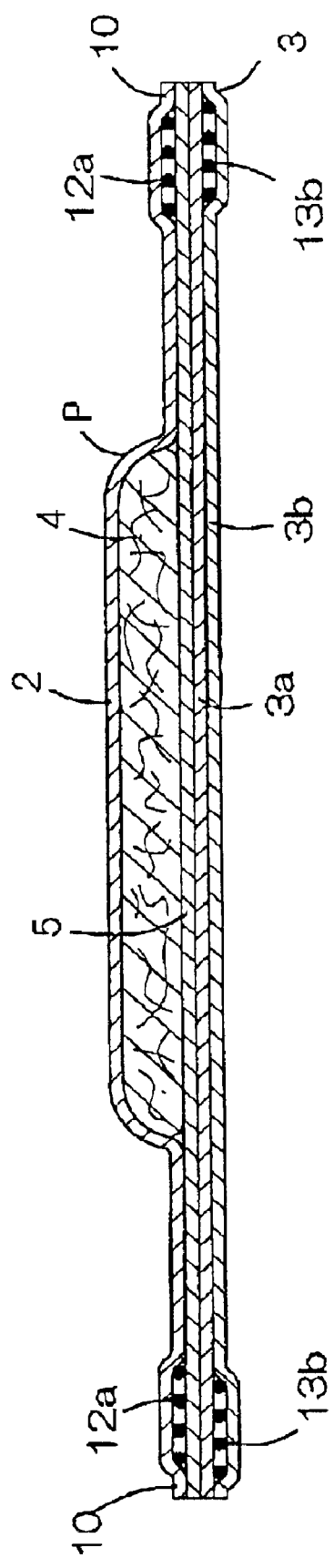
FIG. 3 is a sectional view taken along a line A—A in FIG. 1.
Figure 4:
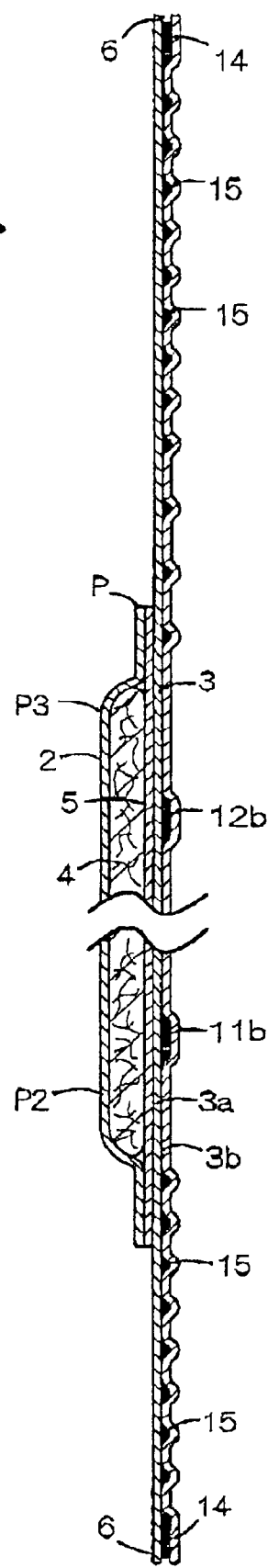
FIG. 4 is a sectional view taken along a line B—B in FIG. 1 with a middle zone of a panel eliminated.

FIG. 1 is a partially cutaway plan view showing a diaper 1A before it is shaped in pants-type, FIG. 2 is a partially cutaway perspective view showing the diaper 1A having been shaped in pants-type from the state of FIG. 1, FIG. 3 is a sectional view taken along a line A—A in FIG. 1 and FIG. 4 is a sectional view taken along a line B—B in FIG. 1 with a middle zone P2 of a panel P eliminated. In FIG. 1, a transverse direction is indicated by an arrow X and a longitudinal direction is indicated by an arrow Y. In FIG. 2, a waist-surrounding direction is indicated by an arrow X and a thigh-surrounding direction is indicated by an arrow Y. Surfaces of top- and backsheets 2, 3 as well as a leak-barrier sheet 5 facing an absorbent core 4 will be referred to herein as inner surfaces thereof and surfaces of these sheets 2, 3, 5 not facing the core 4 will be referred to herein as outer surfaces thereof.

A diaper 1A basically comprises the liquid-absorbent panel P and a liquid-impervious backsheet 3 formed of a composite sheet composed of a plastic film 3b joined to a hydrophobic fibrous nonwoven fabric 3a.

The diaper 1A is composed, in the longitudinal direction, of a front waist region 30, a rear waist region 32 and a crotch region 31 extending between the waist regions 30, 32. The diaper 1A has longitudinally opposite end portions 6 transversely extending in the front and rear trunk regions 30, 32 and transversely opposite side edge portions 7, 8 longitudinally extending in the front and rear waist regions 30, 32. Specifically the diaper 1A is formed by the backsheet 3 of hourglass-shape 3 defining the front and rear waist regions 30, 32 and the crotch region 31 and the panel P attached to the inner surface of the backsheet 3 in the crotch region 31 and extending in the longitudinal direction.

The panel P comprises the liquid-pervious topsheet 2, the liquid-impervious backsheet 3 and a liquid-absorbent core 4 disposed between the topsheet 2 and the leak-barrier sheet 5 and joined to these sheets 2, 5.

The panel P presents an hourglass-shape smaller than that presented by the backsheet 3 and has a front zone P1, a rear zone P3 and a middle zone P2 extending between the front and rear zones P1, P3. Transversely opposite side edge portions 9 of the panel P curve to describe circular arcs which are convex inward as viewed in the transverse direction of the diaper 1A. The panel P is joined to the nonwoven fabric 3a with the leak-barrier sheet 5 lying therebetween.

The topsheet 2 and the leak-barrier sheet 5 have peripheral portions thereof extending outward slightly beyond a peripheral edge of the core 4 and put flat and joined together along the peripheral portions thereof.

Transversely opposite side edge portions of the crotch region 31 partially define transversely opposite side edge portions 10 curving inward transversely so that the portions 10 define the peripheral edge portions of respective leg-openings. The crotch region 31 is provided with elastically stretchable first, second and third elastic members 11, 12, 13 each comprising a plurality of elastic elements secured under tension to the crotch region 31. The front and rear waist regions 30, 32 are respectively provided with elastically stretchable elastic members 14 associated with the waist-opening and auxiliary elastic members 15 each comprising a plurality of elastic elements bonded under tension to the waist regions 30, 32.

The first elastic member 11 extends substantially in a circular arc from respective front ends 10a of the transversely opposite side edge portions 10 lying in the front waist region 30 rearward longitudinally. The first elastic member 11 comprises side portions 11a extending along the transversely opposite side edges 10 in the vicinity of the front ends 10a thereof and a middle portion 11b extending across the front end zone P1 of the panel P.

The second elastic member 12 extends substantially in a circular arc from respective rear ends 10b of the transversely opposite side edge portions 10 lying in the rear waist region 32 forward longitudinally. The second elastic member 12 comprises side portions 12a extending along the transversely opposite side edges 10 in the vicinity of the rear ends 10b thereof and a middle portion 12b spaced rearward from the middle portion 11b of the first elastic member 11 by a given dimension in the longitudinal direction and extending across the rear end zone P3 of the panel P.

The elastic members 14 associated with the waist-opening extend along the longitudinally opposite end portions 6 in the transverse direction. The auxiliary elastic member 15 extends in the transverse direction between the first and second elastic members 11, 12, on one hand and the elastic members 14 associated with the waist-opening, on the other hand. The elastic members 11, 12, 13, 14, 15 are disposed between the nonwoven fabric 3a and the plastic film 3b forming together the backsheet 3 and secured to them.

The third elastic members 13 are attached to the transversely opposite side edge portions 10 of the panel P and extend in the longitudinal direction so as to describe circular arcs which are convex inward as viewed in the transverse direction of the diaper 1A. The third elastic members 13 respectively have connecting portions 13a extending in the front zone P1 of the panel P and connecting portions 13b extending in the rear zone P3 of the panel P. The third elastic members 13 are disposed between the topsheet 2 and the leak-barrier sheet 5 and secured to inner surfaces of these sheets 2, 5.

The connecting portions 13a respectively extend from the associated branching points 16 between the side portions 11a and the middle portions 11b of the respective first elastic members 11 to overlap the respective side portions 11a and extend together with the side portions 11a toward the front ends 10a of the opposite side edge portions 10. The connecting portions 13b respectively extend from the associated branching points 17 between the side portions 12a and the middle portions 12b of the respective first elastic members 12 to overlap the respective side portions 12a and extend together with the side portions 12a toward the rear ends 10b of the opposite side edge portions 10.

In the diaper 1A, the connecting portions 13a, 13b overlap the transversely opposite side edge portions 11a, 12a in this manner and thereby the first and second elastic members 11, 12 are substantially merged into the third elastic members 13 on the transversely opposite side edge portions 10. Consequently, the diaper 1A is formed on the transversely opposite side edge portions 1A with zones 18, 19 in which the elastic members 11, 12, 13 extend together.

As shown in FIG. 2, the front and rear waist regions 30, 32 are joined to each other along transversely opposite side edge portions 7, 8 of the waist regions 30, 32 by means of joining zones 20 arranged intermittently in the longitudinal direction to shape the diaper 1A in pants-type. A waist-opening 21 and a pair of leg-openings 22 are defined as the diaper 1A is shaped in pants-type in this manner. Of the diaper 1A, the longitudinally opposite end portions 6 define a peripheral edge portion of the waist-opening 21 and the transversely opposite side edge portions 10 define peripheral edge portions of the respective leg-openings 22.

The side portions 11a, 12a of the first and second elastic members 11, 12 and the third elastic members 13 extend in the thigh-surrounding direction along the peripheral edge portions of the leg-openings 21. The elastic member 14 associated with the waist-opening extends in a waist-surrounding direction along the peripheral edge portion of the waist-opening 21. The auxiliary elastic members 15 extend in the waist-surrounding direction across the front and rear waist regions 30, 32. In the diaper 1A, a plurality of gathers are formed along the peripheral edge portions of the waist- and leg-openings 21, 22 as well as in the front and rear waist regions 30, 32 as the elastic members 11, 12, 13, 14 contract.

In the zones 18, 19 of the diaper 1A, the side portions 11a, 12a and the connecting portions 13a, 13b extend together, so that the tensile stress in the zones 17, 18 is higher than that in the remaining zone in which the first-third elastic members 11, 12, 13 extend. In this way, the diaper 1A allows the zones 17, 18 of the transversely opposite side edge portions to be placed against the wearer's thighs thereby to be kept in close contact with the wearer's thighs during use of the diaper 1A.

Figure 5:
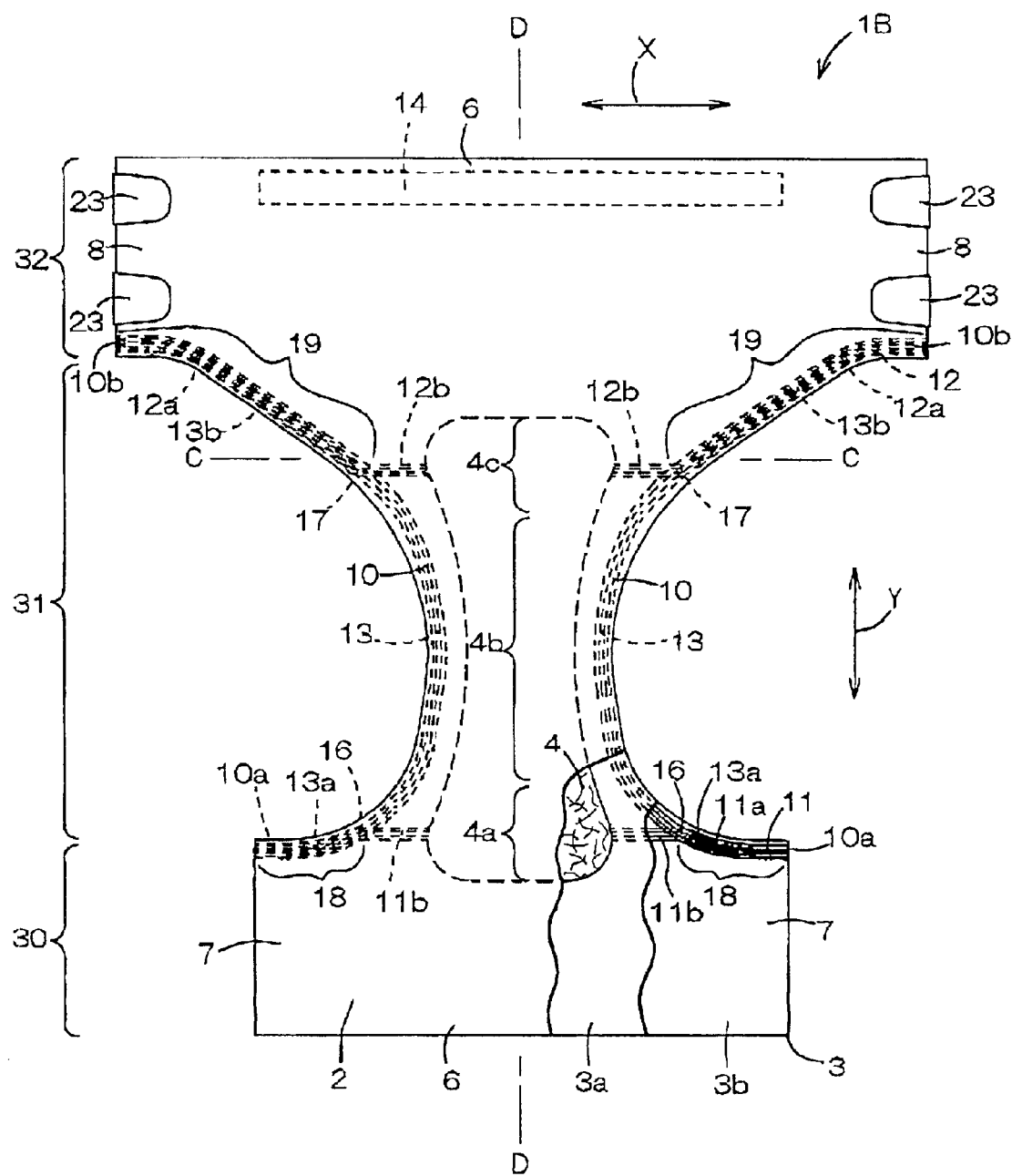
FIG. 5 is a partially cutaway plan view showing an open-type diaper.
Figure 6:
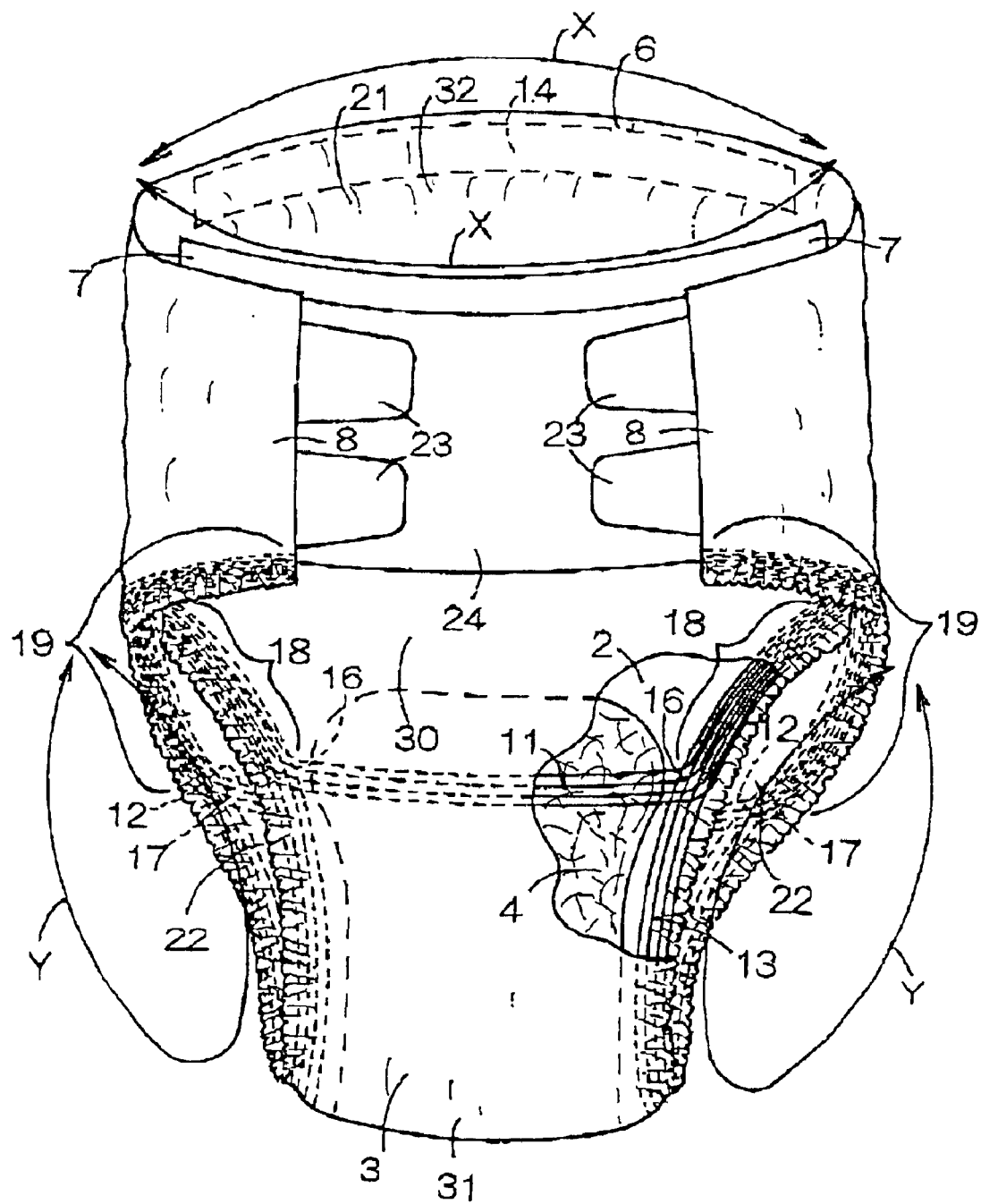
FIG. 6 is a partially cutaway perspective view showing the diaper with its front and rear waist regions connected together to wear the diaper.
Figure 7:
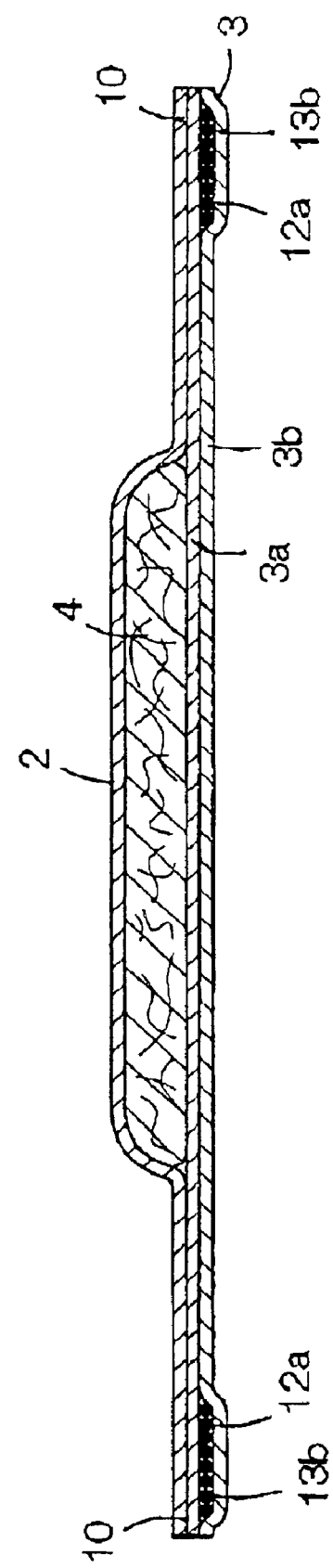
FIG. 7 is a sectional view taken along a line C—C in FIG. 5.
Figure 8:
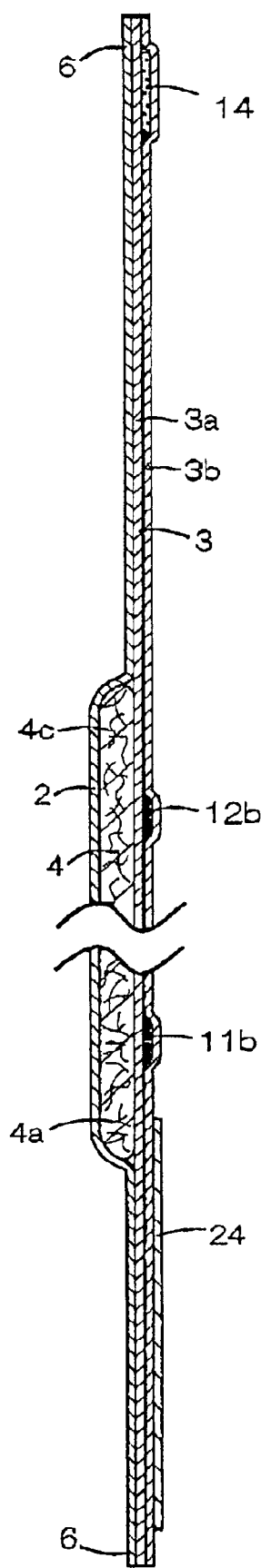
FIG. 8 is a sectional view taken along a line D—D in FIG. 5 with a middle zone of an absorbent eliminated.

FIG. 5 is a partially cutaway plan view showing an open-type diaper 1B, FIG. 6 is a partially cutaway perspective view showing the diaper 1B with the front and rear waist regions 30, 32 connected to each other to be ready for wearing, FIG. 7 is a sectional view taken along a line C—C in FIG. 5 and FIG. 8 is a sectional view taken along a line D—D in FIG. 5 with the middle zone 4b of the core eliminated. In FIG. 5, a transverse direction is indicated by an arrow X and a longitudinal direction is indicated by an arrow Y. In FIG. 6, a waist-surrounding direction is indicated by an arrow X and a leg-surrounding direction is indicated by an arrow Y.

The diaper 1B basically comprises a liquid-pervious topsheet 2, a liquid-impervious backsheet 3 composed of a plastic film 3b joined to a hydrophobic fibrous nonwoven fabric 3a and a liquid-absorbent core 4 disposed between these sheets 2, 3 and entirely covered with tissue paper (not shown) and joined thereto.

The liquid-absorbent core 4 extends in the longitudinal direction in the crotch region 31 and comprises front and rear end zones 4a, 4c and a middle zone 4b extending between these two end zones 4a, 4c. The core 4 is disposed between the top- and backsheets 2, 3 and joined to inner surfaces of these sheets 2, 3 with the tissue paper lying therebetween.

Transversely opposite side edge portions of the crotch region 31 partially define transversely opposite side edge portions 10 curving inward transversely of the diaper 1B so that the portions 10 are destined to define the peripheral edge portions of respective leg-openings. The crotch region 31 is provided with a first elastic member 11 extending substantially in a circular arc from front ends 10a of the transversely opposite side edge portions 10 rearward as viewed in the longitudinal direction and a second elastic member 12 extending substantially in a circular arc from rear ends 10b of the transversely opposite side edge portions 10 forward as viewed in the longitudinal direction, both of these elastic members 11, 12 being attached under tension to the crotch region 31. The crotch region 31 further includes third elastic members 13 extending in the longitudinal direction between the first and second elastic members 11, 12 and secured under tension to the crotch region 31.

The first and second elastic members 11, 12 respectively comprise side portions 11a, 12a extending along the transversely opposite side edge portions 10 in the vicinity of the front and rear ends 10a, 10b thereof and middle portions 11b, 12b spaced apart from each other by a given dimension in the longitudinal direction and extending across the front and rear end zones 4a, 4c of the core 4.

The third elastic members 13 extend in the longitudinal direction so as to describe circular arcs which are convex inward as viewed in the transverse direction of the diaper 1B. The third elastic members 13 respectively have connecting portions 13a extending from respective branching points 16 between the side portions 11a and the middle portion 11b of the first elastic member 11 so as to be merged into the side portions 11a and connecting portions 13b extending from respective branching points 17 between the side portions 12a and the middle portion 12b of the second elastic member 12 so as to be merged into the side portions 12a. The connecting portions 13a extend together with the side portions 11a to the respective front ends 10a of the transversely opposite side edge portions 10. The connecting portions 13b extend together with the side portions 12a to the respective rear ends 10b of the transversely opposite side edge portions 10.

A ribbon-like elastic member 14 associated with the waist-opening is attached under tension to the rear waist region 32 along its longitudinal end portion 6. The elastic members 11, 12, 13, 14 are disposed between the nonwoven fabric 3a and the plastic film 3b and joined to them.

The transversely opposite side edge portions 8 of the rear waist region 32 are provided with tape fasteners 23 extending inward transversely. The tape fasteners 23 respectively have proximal end portions disposed between the nonwoven fabric 3a and the plastic film 3b and bonded to them. Free end portions of the respective tape fasteners 23 are coated with pressure-sensitive adhesive (not shown).

The front waist region 30 is provided on the outer surface of the backsheet 3 with a rectangular target tape strip 24 made of a plastic film. This target tape strip 24 serves as a landing zone for the tape fasteners 23.

To wear this diaper 1B, the transversely opposite side edge portions 8 of the rear waist region 32 are placed upon outer sides of the transversely opposite side edge portions 7 of the front waist region 30 and the free end portions of the tape fasteners 23 are anchored to the target tape strip 24 by means of pressure-sensitive adhesive to connect the front waist region 30 with the rear waist region 32. With the front and rear waist regions 30, 32 connected to each other, the diaper 1B defines, as seen in FIG. 5, a waist-opening 21 and a pair of leg-openings 22.

The transversely opposite side edge portions 10 of the diaper 1B are formed with zones 18, 19 in which the side portions 11a, 12a extend together with the connecting portions 13a, 13b, respectively. In the diaper 1B, the stretch stress in the zones 18, 19 is higher than that in the remaining zone in which the first-third elastic members 11, 12, 13 extend. In this way, the diaper 1B allows the zones 18, 19 of the transversely opposite side edge portions 10 to be placed against the wearer's thighs and thereby to be kept in close contact with the wearer's thighs during use of the diaper 1B.

In the diaper 1A as well as in the diaper 1B have been illustrated and described above, the third elastic members 13 extend along the transversely opposite side edge portions 10 so as to describe circular arcs which are convex inward as viewed in the transverse direction of the diaper 1A, 1B. The third elastic members 13 thus extend in the thigh-surrounding direction around the wearer's thighs as the diaper 1A, 1B is worn. The tensile stress of the third elastic members 13 is effectively exerted on the wearer's thighs and adequately utilized to ensure desired fitness of the diaper 1A, 1B around the wearer's thighs.

In both embodiments of diaper 1A, 1B, the first and second elastic members 11, 12 extend continuously with the third elastic members 13 to surround the wearer's thighs thereby to seal full circumferences of the respective thighs of the wearer. In this way, leakage of excretion possibly occurring in the crotch region 31 is reliably avoided although the first and second elastic members 11, 12 are spaced from each other in the crotch region 31.

In both embodiments of diaper 1A, 1B, the front and rear zones P1, P3 of the panel P or the front and rear zones 4a, 4c of the core 4 are placed against the wearer's skin as the middle portions 11b, 12b of the first and second elastic members 11, 12 contract. In this way, the front and rear zones P1, P3, 4a, 4c are reliably kept in close contact with the wearer's skin.

The topsheet 2 may be formed of a hydrophilic fibrous nonwoven fabric or porous plastic film. The leak-barrier sheet 17 may be formed of a liquid-impervious plastic film. Stock material for the backsheet 3 is not limited to the composite sheet composed of the hydrophobic fibrous nonwoven fabric 3a and the plastic film 3b joined to the hydrophobic fibrous nonwoven fabric 3a. In addition to such composite sheet, the stock material may be selected from a group including a hydrophobic fibrous nonwoven fabric, a liquid-impervious plastic film and laminated two layers of a hydrophobic fibrous nonwoven fabric. The leak-barrier sheet 5 may be formed of a hydrophobic fibrous nonwoven fabric or a liquid-impervious plastic film.

It is also possible to form the backsheet 3 with a composite nonwoven fabric composed of a melt blown fibrous nonwoven fabric having high water-resistance and two layers of a spun bond fibrous nonwoven fabric having high strength and flexibility.

The nonwoven fabric may be selected from a group including spun lace-, needle punch-, melt blown-, thermal bond-, spun bond-, chemical bond- and air through-nonwoven fabrics. The component fibers of the nonwoven fabric may be selected from a group including polyolefine, polyester and polyamide fibers, and polyethylene/ polypropylene or polyethylene/polyester core-sheath-type or side-by-side type conjugated fibers.

The liquid-absortbent core 4 is formed of a mixture of fluff pulp fibers and superabsorbent polymer particles or a mixture of fluff pulp fibers, superabsorbent polymer particles and thermoplastic synthetic resin fibers compressed to a desired thickness. The polymer contained in the core 4 may be selected from a group including a starch- and cellulose-based polymer and a synthetic polymer. The first, second elastic members 11, 12, the third elastic members 13, the elastic member 14 associated with the waist-opening and the auxiliary elastic member 15 may be made of elastomer such as synthetic or natural rubber.

Joining of the sheets 2, 3, 5 to one other, fixing of the core 4, attachment of the elastic members 11, 12, 13, 14, 15 may be carried out using hot melt adhesive or heat welding technique such as heat-sealing or sonic sealing.

Application of this invention is not limited to disposable diapers such as the embodiments 1A, 1B. This invention is applicable also to training pants for baby adapted to promote freedom from a diaper or to a diaper cover adapted to be combined with a liquid-absorbent pad detachably attached to its inner surface.

With the disposable wearing article according to this invention, the third elastic members extend along the transversely opposite side edge portions so as to describe circular arcs which are convex inward as viewed in the transverse direction of the article. This feature enables the third elastic members to extend in the thigh-surrounding direction as the article is worn. With this article, the stretch stress of the third elastic members is exerted around the wearer's thighs and adequately utilized to keep the transversely opposite side edge portions in close contact with the wearer's thighs.

With the article according to this invention, the connecting portions of the third elastic members are merged into the side portions of the first and second elastic members and the stretch stress in the zones in which these elastic members extend together is higher than that in the remaining zone in which these elastic members extend. This feature enables these zones to be tightly placed against the wearer's thighs. With the article according to this invention, it is possible to keep the transversely opposite side edge portions in close contact with the wearer's thighs in these zones extending from the vicinity of the respective branching points between the side portions of the first and second elastic members, on one hand, and the middle portions thereof, on the other hand, to the vicinity of the front and rear ends of the transversely opposite side edge portions.

What is claimed is:

1. A disposable undergarment, comprising:
   a front waist region, a rear waist region and a crotch region extending longitudinally of said undergarment between the front and rear waist regions, said crotch region having transversely opposite side edges curving inward transversely of said undergarment to define peripheral edges of leg-openings of said undergarment;
   first and second elastic members each including opposite end portions and a middle portion disposed between and connecting the end portions;
   each of the end portions of the first elastic member extending along a front end portion of one of said transversely opposite side edges of said crotch region, the middle portion of the first elastic member extending across said crotch region;
   each of the end portions of the second elastic member extending along a rear end portion of one of said transversely opposite side edges of said crotch region, the middle portion of the second elastic member extending across said crotch region;

the first and second elastic members being completely spaced apart in a longitudinal direction of said undergarment without contacting or crossing each other;

a pair of third elastic members each extending along one of said transversely opposite side edges of said crotch region and curving inward transversely of said undergarment;

each of said third elastic members having a front portion extending alongside at least a part of one of the end portions of the first elastic member, and a rear portion extending alongside at least a part of one of the end portions of the second elastic member;

wherein a tensile stress of overlapping zones in which the front and rear portions of said third elastic members extend alongside the respective end portions of said first and second elastic members is higher than that of non-overlapping zones in which said first, second and third elastic members do not extend alongside each other;

said disposable undergarment further comprising:
a liquid-absorbent panel including a liquid-absorbent core disposed between a liquid-pervious topsheet and a leak-barrier sheet; and
a liquid-impervious backsheet;

said panel being joined to said backsheet with said leak-barrier sheet lying between the backsheet and the core;

said first and second elastic members being attached to said backsheet; and said third elastic members being attached to transversely opposite side edge portions of said panel extending along said transversely opposite side edges of said crotch region.

2. The undergarment according to claim 1, wherein an entire area of said topsheet is smaller than that of said backsheet.

3. The undergarment according to claim 2, wherein said third elastic members terminate at an edge of said topsheet.

4. A disposable undergarment, comprising:
a front waist region, a rear waist region and a crotch region extending longitudinally of said undergarment between the front and rear waist regions, said crotch region having transversely opposite side edges curving inward transversely of said undergarment to define peripheral edges of leg-openings of said undergarment;

first and second elastic members each including opposite end portions and a middle portion disposed between and connecting the end portions;

each of the end portions of the first elastic member extending along a front end portion of one of said transversely opposite side edges of said crotch region, the middle portion of the first elastic member extending across said crotch region;

each of the end portions of the second elastic member extending along a rear end portion of one of said transversely opposite side edges of said crotch region, the middle portion of the second elastic member extending across said crotch region;

the first and second elastic members being completely spaced apart in a longitudinal direction of said undergarment without contacting or crossing each other;

a pair of third elastic members each extending along one of said transversely opposite side edges of said crotch region and curving inward transversely of said undergarment;

each of said third elastic members having a front portion extending alongside at least a part of one of the end portions of the first elastic member, and a rear portion extending alongside at least a part of one of the end portions of the second elastic member;

wherein a tensile stress of overlapping zones in which the front and rear portions of said third elastic members extend alongside the respective end portions of said first and second elastic members is higher than that of non-overlapping zones in which said first, second and third elastic members do not extend alongside each other; and wherein said backsheet has at least two material layers including an upper layer and a lower layer, said first and second elastic members are sandwiched between said upper and lower layers, and said third elastic members are sandwiched between said upper layer and said topsheet.

5. A disposable undergarment comprising:
a front waist region, a rear waist region and a crotch region extending longitudinally of said undergarment between the front and rear waist regions, said crotch region having transversely opposite side edges curving inward transversely of said undergarment to define peripheral edges of leg-openings of said undergarment;

first and second elastic members each including opposite end portions and a middle portion disposed between and connecting the end portions;

each of the end portions of the first elastic member extending along a front end portion of one of said transversely opposite side edges of said crotch region, the middle portion of the first elastic member extending across said crotch region;

each of the end portions of the second elastic member extending along a rear end portion of one of said transversely opposite side edges of said crotch region, the middle portion of the second elastic member extending across said crotch region;

the first and second elastic members being completely spaced apart in a longitudinal direction of said undergarment without contacting or crossing each other;

a pair of third elastic members each extending along one of said transversely opposite side edges of said crotch region and curving inward transversely of said undergarment;

each of said third elastic members having a front portion extending alongside at least a part of one of the end portions of the first elastic member, and a rear portion extending alongside at least a part of one of the end portions of the second elastic member;

wherein a tensile stress of overlapping zones in which the front and rear portions of said third elastic members extend alongside the respective end portions of said first and second elastic members is higher than that of non-overlapping zones in which said first, second and third elastic members do not extend alongside each other; and wherein each of said third elastic members extends alongside an entirety of each of the respective end portions of said first and second elastic members.

6. A disposable undergarment, comprising:
a front waist region, a rear waist region and a crotch region extending longitudinally of said undergarment between the front and rear waist regions, said crotch region having transversely opposite side edges curving inward transversely of said undergarment to define peripheral edges of leg-openings of said undergarment;

first and second elastic members each including opposite end portions and a middle portion disposed between and connecting the end portions;

each of the end portions of the first elastic member extending along a front end portion of one of said transversely opposite side edges of said crotch region, the middle portion of the first elastic member extending across said crotch region;

each of the end portions of the second elastic member extending along a rear end portion of one of said transversely opposite side edges of said crotch region, the middle portion of the second elastic member extending across said crotch region;

the first and second elastic members being completely spaced apart in a longitudinal direction of said undergarment without contacting or crossing each other;

a pair of third elastic members each extending along one of said transversely opposite side edges of said crotch region and curving inward transversely of said undergarment;

each of said third elastic members having a front portion extending alongside at least a part of one of the end portions of the first elastic member, and a rear portion extending alongside at least a part of one of the end portions of the second elastic member;

wherein a tensile stress of overlapping zones in which the front and rear portions of said third elastic members extend alongside the respective end regions of said first an second elastic members is higher than that of non-overlapping zones in which said first, second and third elastic members do not extend alongside each other; and wherein at least one of said first and second elastic members includes a plurality of stretchable strands extending in parallel, and at least one of the front and rear portions of said third elastic members terminate at a point located between adjacent said strands.

7. A disposable undergarment, comprising:

a front waist region, a rear waist region and a crotch region extending longitudinally of said undergarment between the front and rear waist regions, said crotch region having transversely opposite side edges curving inward transversely of said undergarment to define peripheral edges of leg-openings of said undergarment;

first and second elastic members each including opposite end portions and a middle portion disposed between and connecting the end portions;

each of the end portions of the first elastic member extending along a front end portion of one of said transversely opposite side edges of said crotch region, the middle portion of the first elastic member extending across said crotch region;

each of the end portions of the second elastic member extending along a rear end portion of one of said transversal opposite side edges of said crotch region the middle portion of a elastic member extending across said crotch region;

the first and second elastic members being completely spaced apart in a longitudinal direction of said undergarment without contacting or crossing each other;

a pair of third elastic members each extending along one of said transversely opposite side edges of said crotch region and curving inward transversal of said undergarment;

each of said third elastic members having a front portion extending alongside at least a part of one of the end portions of the first elastic member, and a rear portion extending alongside at least a part of one of the end portions of the second elastic member;

wherein a tensile stress of overlapping zones in which the front and rear portions of said third elastic members extend alongside the respective end portions of said first and second elastic members is higher than that of non-overlapping zones in which said first, second and third elastic members do not extend alongside each other;

said disposable undergarment further comprising a liquid-pervious topsheet, a liquid-impervious backsheet and a liquid-absorbent core disposed between the topsheet and backsheet, wherein said core includes a front end zone, a rear end zone, and a middle zone extending longitudinally of said undergarment between the front and rear end zones, said middle zone being completely located in said crotch region, said front end zone extending from said middle zone toward said front waist region, and said rear end zone extending from said middle zone toward said rear waist region; and the middle portions of said first and second elastic members underlie the front and rear end zones of said core, respectively.

\* \* \* \* \*